United States Patent [19]

Berger

[11] Patent Number: 4,721,726

[45] Date of Patent: Jan. 26, 1988

[54] SUBSTITUTED DIPEPTIDES AS INHIBITORS OF ENKEPHALINASES

[75] Inventor: Joel G. Berger, Cedar Grove, N.J.

[73] Assignee: Schering Corporation, Kenilworth, N.J.

[21] Appl. No.: 890,667

[22] Filed: Jul. 25, 1986

Related U.S. Application Data

[63] Continuation-in-part of Ser. No. 621,021, Jun. 15, 1984, Pat. No. 4,610,816, which is a continuation-in-part of Ser. No. 483,463, Apr. 11, 1983, abandoned, which is a continuation-in-part of Ser. No. 444,761, Nov. 26, 1982, abandoned, which is a continuation-in-part of Ser. No. 258,485, Apr. 28, 1981, abandoned, which is a continuation-in-part of Ser. No. 217,621, Dec. 18, 1980, abandoned.

[51] Int. Cl.$^4$ .................. A61K 31/195; A61K 31/24; A61K 31/34

[52] U.S. Cl. .................. 514/464; 514/467; 514/533; 514/547; 514/566

[58] Field of Search .............. 514/464, 467, 533, 547, 514/566

[56] References Cited

U.S. PATENT DOCUMENTS 4,610,816  9/1986  Berger .................. 549/452

*Primary Examiner*—Delbert R. Phillips
*Attorney, Agent, or Firm*—James R. Nelson; Stephen I. Miller; Gerald S. Rosen

[57] ABSTRACT

A method for inhibiting the action of enkephalinases in a mammal to thereby elicit an analgesic effect in said mammal is described.

Novel compound and compositions useful for accomplishing the method of the invention are also described.

15 Claims, No Drawings

SUBSTITUTED DIPEPTIDES AS INHIBITORS OF ENKEPHALINASES

This application is a continuation-in-part of application Ser. No. 621,021, filed June 15, 1984, now U.S. Pat. No. 4,610,816 filed Sept. 9, 1986; which was a continuation-in-part of application Ser. No. 483,463, filed Apr. 11, 1983 abandoned; which in turn was a continuation-in-part of application Ser. No. 444,761, filed Nov. 26, 1982 now abandoned; which in turn was a continuation-in-part of application Ser. No. 258,485, filed Apr. 28, 1981 now abandoned; which in turn was a continuation in part of application Ser. No. 217,621, filed Dec. 18, 1980 now abandoned.

BACKGROUND OF THE INVENTION

Enkephalin is a natural opiate receptor against and is believed to be a mixture of two pentapeptides: H-Tyr-Gly-Gly-Phe-Met-OH (methionine-enkephalin), and H-Tyr-Gly-Gly-Phe-Leu-OH (leucine-enkephalin). Hereinafter, the name enkephalin is used generically to embrace all such compounds.

It has been reported by Beluzzi et.al., Nature, 260, 625 (1976), that when enkephalin is injected into the brain ventricle of rats, a profound analgesia is obtained. It is also known in the art that enkephalin is acted upon by a group of enzymes known generically as enkephalinases, which are also naturally occurring and is inactivated thereby. The present invention provides a method for inhibiting the action of enkephalinases, and compounds useful for accomplishing said method.

European Patent Application No. 79105015.6, publication No. 12401 discloses certain dipeptide derivatives which are described as possessing antihypertensive effects.

SUMMARY OF THE INVENTION

The invention sought to be patented in its pharmaceutical method aspect is a method for inhibiting the action of enkephalinases in a mammal to thereby elicit an analgesic effect in said mammal, which method comprises administering an enkephalinase inhibitory effective amount of a compound having structural formula I $$R_1C^*H(COR_2)-NH-C^*HR_3-CONH(CH_2)_p-C^*(R_4R_5)-COR_6 \quad I$$

and the racemates, enantiomers and diastereoisomers thereof and the pharmaceutically acceptable salts thereof to said mammal wherein:

$R^1$ is alkyl having from 1 to 6 carbon atoms, adamantylmethyl, cycloakylmethyl having from 4 to 8 carbon atoms or $A-X_m-C_nH_{2n}-$ wherein X is oxygen or sulfur, A is phenyl which may be substituted with the group, Y, wherein Y is halogen, hydroxy, trifluoromethyl, alkoxy having from 1 to 6 carbon atoms, alkyl having from 1 to 6 carbon atoms, 2- and 3-furanyl, 2- and 3-thienyl, or phenyl {which may be substituted with halogen, hydroxy, trifluoromethyl, alkoxy having from 1 to 6 carbon atoms or alkyl having from 1 to 6 carbon atoms} benzyl {the phenyl ring of which may be substituted with the group, Y, as defined herein}, 1- and 2-naphthyl, 2-and 3-furanyl or 2- and 3-thienyl; m is 0 or 1 and n is 0, 1, 2, 3, or 4;

$R_2$ and $R_6$ may be the same or different and are hydroxy, alkoxy having from 1 to 8 carbon atoms, $B-X_m-C_nH_{2n}-O-$ wherein B is phenyl {which may be substituted with the group, Y, as defined herein} or 1- and 2-naphthyl, X, m, and n are as defined herein provided that when n=0, m=0, —OCH₂OCO—alkyl having from 3 to 8 carbon atoms, —OCH₂CO-phenyl {the phenyl ring of which may be substituted with the group, Y, as defined herein}, 1-glyceryl,

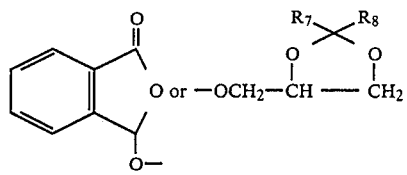

wherein $R_7$ is hydrogen, alkyl having from 1 to 6 carbon atoms, or phenyl which may be substituted with the group, Y, as defined herein, and $R_8$ is hydrogen or alkyl having from 1 to 6 carbon atoms;

$R_2$ may also be $-NR_7R_8$ wherein $R_7$ and $R_8$ are as defined herein;

$R_3$ is alkyl having from 1 to 6 carbon atoms, cycloalkylmethyl having from 4 to 8 carbon atoms, 2- and 3-thienylmethyl, 2- and 3-furanylmethyl, 1- and 2-naphthylmethyl, or benzyl the phenyl ring of which may be substituted with the group, Y, as defined herein;

$R_4$ is $D-C_nH_{2n}-O_m-$ wherein D is hydrogen, alkyl having from 1 to 4 carbon atoms or phenyl which may be substituted with the group, Z, wherein Z is halogen, hydroxy, trifluoromethyl, alkoxy having from 1 to 6 carbon atoms, or alkyl having from 1 to 6 carbon atoms; m and n are as defined herein;

$R^4$ may also be $-NR_5COR_7$ {wherein $R_5$ and $R_7$ are defined herein}, and $-NR_5CO_2R_9$ {wherein $R_5$ is defined herein and $R_9$ is alkyl having from 1 to 6 carbon atoms or phenyl which may be substituted with the group Y, as defined herein} provided that p is 1 or 2;

$R_5$ is hydrogen or alkyl having from 1 to 6 carbon atoms; and p is 0, 1 or 2.

A second method aspect of the invention is a method for treating depression in a mammal comprising administering an antidepressant effective amount of a compound of formula I as defined above to the mammal.

Preferred values for the above-defined groups are as follows:

$R_1$ is benzyl, p-chlorobenzyl, p-methoxybenzyl, p-methylbenzyl, p-phenylbenzyl, 2-phenylethyl or 1- or 2-naphthylmethyl;

$R_2$ and $R_6$ may be the same or different and are hydroxy, methoxy, ethoxy, benzyloxy, 2-phenoxyethoxy, 1-glyceryl,

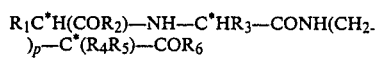 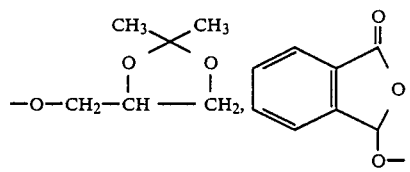

or pivaloyloxymethoxy;

$R_3$ is benzyl, p-methylbenzyl, p-phenylbenzyl, 1-naphthylmethyl or 3-thienylmethyl;

$R_4$ is hydrogen, methyl or benzyl;

$R_5$ is hydrogen; and p is 1 or 2.

The most preferred values for the above defined groups are as follows:

R₁ is benzyl and p-phenylbenzyl;
R₂ is hydroxy, 2-phenoxyethoxy, 1-glyceryl,

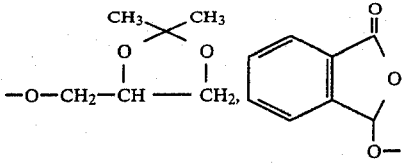

pivaloyloxymethoxy and benzyloxy;
R₃ is benzyl and p-phenylbenzyl;
R₄ is hydrogen, methyl and benzyl;
R₅ is hydrogen;
R₆ is hydroxy; and
p is 1.

Specific compounds having structural formula I contemplated by the invention are those having the names:

N-[N-[(L-1-carboxy-2-phenylethyl)]-L-phenylalanyl]-β-alanine;

N-[N-[L-1(2,2-dimethyl-1-oxopropoxy)-methoxy]carbonyl]-2-phenylethyl]-L-phenylalanyl]-β-alanine, (2,2-dimethyl-1-oxypropoxy)methyl ester;

N-[N-[L-1-[phenylmethoxy]carbonyl]-2-phenyl-ethyl]-L-phenylalanyl]-β-alanine, (2,2-dimethyl-1-oxopropoxy)methylester;

N-[N-[L-1-carboxy-2-(4-phenyl)phenylethyl]-L-phenylalanyl]-β-alanine;

N-[N-[L-[1-[(2,2-dimethyl-1-oxopropoxy)-methoxy]-carbonyl]-2-(4-phenyl)phenylethyl]-L-phenylalanyl]-β-alanine,(2,2-dimethyl-1-oxopropoxy)methyl ester;

N-[N-[L-1-carboxy-2-phenylethyl]-L-(4-phenyl)-phenylalanyl]-β-alanine;

N-[N-[L-[1-[(2,2-dimethyl-1-oxopropoxy)-methoxy]-carbonyl]-2-(4-phenyl)phenylethyl]-L-(4-phenyl)-phenylalanyl-β-alanine, (2,2-dimethyl-1-oxopropoxy)methyl ester;

N-[N-[L-[1-[(2,2-dimethyl-1-oxopropoxy)-methoxy]-carbonyl]-2-phenylethyl]-L-(4-phenyl)phenylalanyl]-β-alanine,(2,2-dimethyl-1-methyl ester;

N-[N-L-1-carboxy-2-phenylethyl]-L-phenylalanyl]-L-(1-methyl)-β-alanine;

N-[N-[L-[1-[(2,2-dimethyl-1-oxopropoxy)methoxy]-carbonyl]-2-phenylethyl]-L-phenylalanyl]-L-(1-methyl)-β-alanine,(2,2-dimethyl-1-oxopropoxy)-methyl ester;

N-[N-[(L-1-carboxy-2-phenylethyl)]-L-phenylalanyl]-β-alanine, 2-phenoxyethyl ester;

N-[N-[(D-1-carboxy-2-phenylethyl)]-L-leucyl]-L-phenylalanine;

N-[N-[(L-1-carboxy-2-phenylethyl)]-L-phenylalanyl]-L-phenylalanine;

N-[N-[(L-1-carboxy-3-phenylpropyl)]-L-phenylalanyl]-β-alanine;

N-[N-[L-[1-[(2,2-dimethyl-1-oxopropoxy)-methoxy]-carbonyl]-2-phenylethyl]-L-phenylalanyl]-β-alanine;

N-[N-[L-[1-[(2-phenoxy)ethoxy]carbonyl]-2-phenylethyl]-L-phenylalanyl]-β-alanine;

N-[N-[L-[1-[(1-oxo-3-isobenzofuranyloxy)]-carbonyl]-2-phenylethyl]-L-phenylalanyl]-β-alanine;

N-[N-[L-[1-[(2,3-dihydroxy)-1-propoxy]-carbonyl]-2-phenylethyl]-L-phenylalanyl]-β-alanine;

N-[N-[L-[1-[(2,2-dimethyl-1,3-dioxolan-4-yl)methoxy]-carbonyl]-2-phenylethyl]-L-phenylananyl]-β-alanine;

N-[N-[L-[1-[(2,2-dimethyl-1-oxypropoxy)methoxy]-carbonyl]-2-(4-phenyl)phenylethyl]-L-phenylalanyl]-β-alanine;

N-[N-[L-[1-[(2-phenoxy)ethoxy]carbonyl]-2-(4-phenyl)-phenylethyl]-L-phenylalanyl]-β-alanine;

N-[N-[L-[1-[(1-oxo-3-isobenzofuranyloxy)]-carbonyl]-2-(4-phenyl)phenylethyl]-L-phenylalanyl]-β-alanine;

N-[N-[L-[1-[(2,3-dihydroxy)-1-propoxy]-car-bonyl]-2-(4-phenyl)phenylethyl]-L-phenylalanyl]-β-alanine;

N-[N-[L-[1-[(2,2-dimethyl-1,3-dioxolan -4-yl)-methoxy]-carbonyl]-2-(4-phenyl)phenylethyl]-L-phenylalanyl]-β-alanine;

N-[N-[L-[1-[(2,2-dimethyl-1-oxypropoxy)methoxy]-carbonyl]-2-phenylethyl]-L-(4-phenyl)phenylalanyl]-β-alanine;

N-[N-[L-[1-[(2-phenoxy)ethoxy]carbonyl]-2-phenylethyl]-L-(4-phenyl)phenylalanyl]-β-alanine;

N-[N-[L-[1-[(1-oxo-3-isobenzofuranyloxy)]-carbonyl]-2-phenylethyl]-L-(4-phenyl)phenylalanyl]-β-alanine;

N-[N-[L-[1-[(2,3-dihydroxy)-1-propoxy]-carbonyl]-2-phenylethyl]-L-(4-phenyl)phenylalanyl]-β-alanine;

N-[N-[L-[1-[(2,2-dimethyl-1,3-dioxolan-4-yl)-methoxy]-carbonyl]-2-phenylethyl]-L-(4-phenyl)phenylalanyl]-β-alanine;

N-[N-[L-[1-[(2,2-dimethyl-1-oxypropoxy)-methoxy]-carbonyl]-2-(4-phenyl)phenylethyl]-L-(4phenyl)-phenylalanyl]-β-alanine;

N-[N-[L-[1-[(2-phenoxy)ethoxy]carbonyl]-2-(4-phenyl)phenylethyl]-L-(4-phenyl)phenylalanyl]-β-alanine;

N-[N-[L-[1-[(1-oxo-3-isobenzofuranyloxy)]-carbonyl]-2-(4-phenyl)phenylethyl]-L-(4-phenyl)phenylalanyl]-β-alanine;

N-[N-[L-[1-[2,3-dihydroxy)-1-propoxy]-carbonyl]-2-(4-phenyl)-phenylethyl]-L-(4-phenyl)-phenylalanyl]-β-alanine;

N-[N-[L-[1-[(2,2-dimethyl-1,3-dioxolan-4-yl)methoxy]-carbonyl]-2-(4-phenyl)phenylethyl]-L-(4-phenyl)-phenylalanyl]-β-alanine;

N-[N-[L-[1-[(2,2-dimethyl-1-oxypropoxy)-methoxy]-carbonyl]-2-phenylethyl]-L-phenylalanyl]-D,L-α-methyl-β-alanine;

N-[N-[L-[1-[(2-phenoxy)ethoxy]carbonyl]-2-phenylethyl]-L-phenylalanyl]-D,L-α-methyl-β-alanine;

N-[N-[L-[1-[(1-oxo-3-isobenzofuranyloxy)]-carbonyl]-2-phenylethyl]-L-phenylalanyl]-D,L-α-methyl-β-alanine;

N-[N-[L-[1-[(2,3-dihydroxy)-1-propoxy]-carbonyl]-2-phenylethyl]-L-phenylalanyl]-D,L-α-methyl-β-alanine;

N-[N-[L-[1-[(2,2-dimethyl-1,3-dioxolan-4-yl)-methoxy]-carbonyl]-2-phenylethyl]-L-phenylalanyl]-D,L-α-methyl-β-alanine;

N-[N-[L-[1-[(2,2-dimethyl-1-oxypropoxy)-methoxy]-carbonyl]-2-(4-phenyl)phenylethyl]-L-phenylalanyl]-D,L-α-methyl-β-alanine;

N-[N-[L-[1-[(2-phenoxy)ethoxy]carbonyl]-2-(4-phenyl)-phenylethyl]-L-phenylalanyl]-D,L-α-methyl-β-alanine;

N-[N-[L-[1-[(1-oxo-3-isobenzofuranyloxy)]-carbonyl]-2-(4-phenyl)phenylethyl]-L-phenylalanyl]-D,L-α-methyl-β-alanine;

N-[N-[L-[1-[(2,3-dihydroxy)-1-propoxy]carbonyl]-2-(4-phenyl)phenylethyl]-L-phenylalanyl]-D,L-α-methyl-β-alanine;

N-[N-[L-[1-[(2,2-dimethyl-1,3-dioxolan-4-yl)-methoxy]-carbonyl]-2-(4-phenyl)phenylethyl]-L-phenyl-alanyl]-D,L-α-methyl-β-alanine;

N-[N-[L-[1-[(2,2-dimethyl-1-oxypropoxy)methoxy]-carbonyl]-2-phenylethyl]-L-(4-phenyl)phenylalanyl]-D,L-α-methyl-β-alanine;

N-[N-[L-[1-[(2-phenoxy)ethoxy]carbonyl]-2-phenylethyl]-L-(4-phenyl)phenylalanyl]-D,L-α-methyl-β-alanine;

N-[N-[L-[1-[(1-oxo-3-isobenzofuranyloxy)]-carbonyl]-2-phenylethyl]-L-(4-phenyl)phenylalanyl]-D,L-α-methyl-β-alanine;

N-[N-[L-[1-[(2,3-dihydroxy)-1-propoxy]-carbonyl]-2-phenylethyl]-L-(4-phenyl)phenylalanyl]-D,L-α-methyl-β-alanine;

N-[N-[L-[1-[(2,2-dimethyl-1,3-dioxolan-4-yl)-methoxy]-carbonyl]-2-phenylethyl]-L-(4-phenyl)phenylalanyl]-D,L-α-methyl-β-alanine;

N-[N-[L-[1-[(2,2-dimethyl-1-oxypropoxy)methoxy]-carbonyl]-2-(4-phenyl)phenylethyl]-L-(4-phenyl)-phenylalanyl]-D,L-α-methyl-β-alanine;

N-[N-[L-[1-[(2-phenoxy)ethoxy]carbonyl]-2-(4-phenyl)-phenylethyl]-L-(4-phenyl)phenylalanyl]-D,L-α-methyl-β-alanine;

N-[N-[L-[1-[(1-oxo-3-isobenzofuranyloxy)]carbonyl]-2-(4-phenyl)phenylethyl]-L-(4-phenyl)phenylalanyl]-D,L-α-methyl-β-alanine;

N-[N-[L-[1-[(2,3-dihydroxy)-1-propoxy]carbonyl]-2-(4-phenyl)phenylethyl]-L-(4-phenyl)phenylalanyl]-D,L-α-methyl-β-alanine;

N-[N-[L-[1-[(2,2-dimethyl-1,3-dioxolan-4-yl)-methoxy]-carbonyl]-2-(4-phenyl)phenylethyl]-L-(4-phenyl)-phenylalanyl]-D,L-α-methyl-β-alanine;

N-[N-[L-[1-[(2,2-dimethyl-1-oxypropoxy)methoxy]-carbonyl]-2-phenylethyl]-L-2-thienylalanyl]-β-alanine;

N-[N-[L-[1-[(2,2-dimethyl-1-oxypropoxy)-methoxy]-carbonyl]-2-phenylethyl]-L-3-thienylalanyl]-β-alanine;

N-[N-[L-[1-[(2,2-dimethyl-1-oxypropoxy)methoxy]carbonyl]-2-phenylethyl]-L-2-furoalanyl]-β-alanine;

N-[N-[L-[1-[(2,2-dimethyl-1-oxypropoxy)methoxy]carbonyl]-2-phenylethyl]-L-phenylalanyl]-α-methylalanine;

N-[N-[L-[1-[(2,2-dimethyl-1-oxypropoxy)methoxy]carbonyl]-2-phenylethyl]-L-phenylalanyl]-L-α-hydroxy-β-alanine;

N-[N-[L-[1-[(2,2-dimethyl-1-oxypropoxy)methoxy]carbonyl]-2-phenylethyl]-L-phenylalanyl]-D-α-hydroxy-β-alanine;

N-[N-[L-[1-[(2,2-dimethyl-1-oxypropoxy)methoxy]carbonyl]-2-phenylethyl]-L-phenylalanyl]-L-α-methoxy-β-alanine;

N-[N-[L-[1-[(2,2-dimethyl-1-oxypropoxy)methoxy]carbonyl]-2-phenylethyl]-L-phenylalanyl]-D-α-methoxy-β-alanine; and N-[N-[L-[1-[(2,2-dimethyl-1,3-dioxolan-4-yl)-methoxy]-carbonyl]-2-phenylethyl]-L-phenylalanyl]-R-α-hydroxy-β-alanine;

N-[N-[L-[1-[(2,2-dimethyl-1,3-dioxolan-4-yl)-methoxy]-carbonyl]-2-phenylethyl]-L-phenylalanyl]-β-alanine, hemimaleate; and N[-[N-[(L-1-carboxy-2-phenylethyl)]-L-phenylalanyl]-S-2-[N-[(1,1-dimethylethoxy)carbonyl]amino-β-alanine.

The invention sought to be patented in its chemical compound aspect is a compound having structural formula I wherein p is 1 or 2 and the racemates, enantiomers and diasteriomers thereof and the pharmaceutically acceptable salts thereof.

The invention contemplates the above-described subgenera and species of compounds having structural formula I, as well as their use in the method of the invention.

The invention sought to be patented in its pharmaceutical composition aspect is a composition useful for providing analgesia, for treating depression or for inhibiting the action of enkephalinases in a mammal, which composition comprises a compound having structural formula I in combination with a pharmaceutically acceptable carrier.

DESCRIPTION OF THE INVENTION

The compounds of this invention way be prepared by using reactions and reagents well known in the polypeptide art. In general, these reactions involve selection or preparation of suitably substituted amino acids, protecting functional groups which may react if left unprotected, condensing the protected or blocked amino acid with a suitable reactant and deprotecting the product. The following Methods may be used to prepare the compounds of this invention from readily available or easily prepared starting materials:

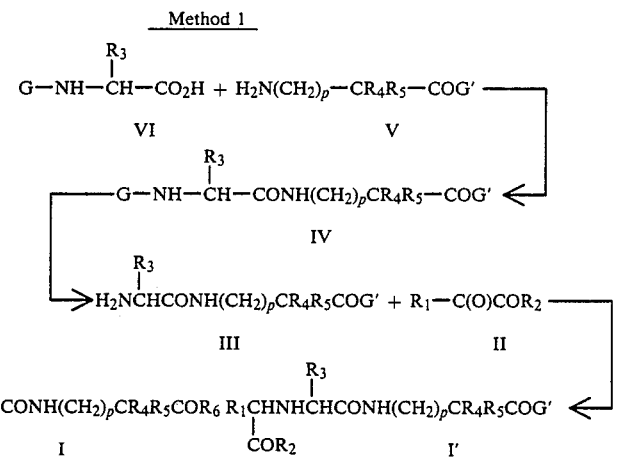

In the foregoing reaction sequence, the amino function of Compound VI is protected by an amino protecting group commonly used in the art (G) such as benzyloxycarbonyl, t-butyloxycarbonyl or the like. Compound VI is condensed with an aminoester derivative V wherein G' is benzyloxy, t-butyloxy, lower alkoxy or the like. Condensing agents such as dicyclohexyl carbodiimide, or diphenylphosphoryl azide may be employed. Also, activating agents such as 1-hydroxybenzotriazole may be employed in the reaction.

The resulting dipeptide IV is deprotected at the amine terminus by treatment with acids or by hydrogenation using for example, hydrogen and a metal catalyst. The resulting product, (III), is then condensed with a ketoacid or ketoester (II) in a suitable solvent such as water or acetonitrile at a substantially neutral pH in the presence of a reducing agent such as sodium cyanoborohydride or other equivalently functioning reducing agent. Alternatively, the Schiff base resulting from the initial condensation of II and III may be catalytically reduced to give I using hydrogen at a pressure of 1-4 atmospheres. The catalytic reduction may be effected using Raney nickel catalyst or 10% palladium on carbon or the like. The compounds of this invention having a terminal carboxyl group may be prepared from a corresponding ester by hydrolysis or hydrogenolysis.

In the foregoing reaction sequence, substituents $R_1$, $R_2$, $R_3$, $R_4$, $R_5$ and $R_6$; and p are as previously defined, G and G' are suitable amine protecting groups.

Method 2

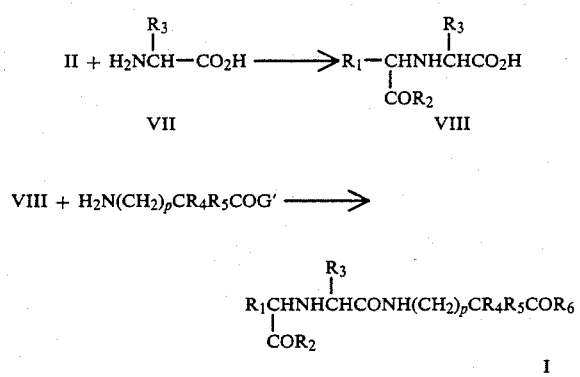

Method 2 is commenced by condensing an $R_3$ substituted aminoacid with a ketoester II by procedures substantially as described in Method 1. The resulting intermediate (VIII) is then coupled with an $R_4$, $R_5$ substituted amino acid wherein the carboxy group is derivatized by a lower alkoxy, or a dialkylamino group, or an equivalently acting group G' to form compounds which after removal of protecting groups which may be present will produce products of this invention wherein substituents $R_1$, $R_2$, $R_3$, $R_4$, $R_5$ and $R_6$; and p are as defined above.

Method 3

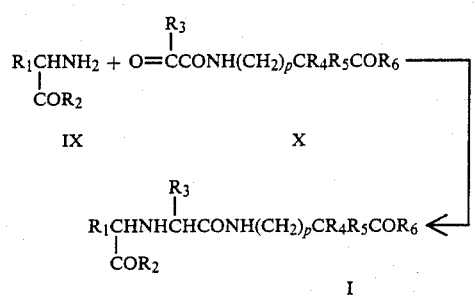

An amino acid or ester (IX) wherein $R_1$ and $R_2$ have been defined as above is condensed with a carbonyl compound (X) under conditions described in Methods 1 and 2 to prepare I. Substituents $R_3$, $R_4$, $R_5$ and $R_6$; and p are as previously described.

Method 4

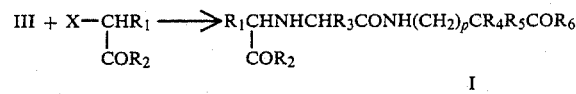

Intermediate III, whose preparation is shown in Method 1, is reacted with a substituted halo ester under conventional alkylating conditions, preferably in the presence of a base (a tertiary amine or an inorganic hydroxide, carbonate or bicarbonate). The reaction is usually carried out in water or in an organic solvent, such as N,N-dimethylformamide or acetonitrile. Substituents $R_1$, $R_2$, $R_3$, $R_4$, $R_5$ and $R_6$; and p are as previously described.

In the foregoing reaction sequences wherein water is generated by the reactants (e.g. the condensation of compounds II and III in Method 1), the reaction may be effected by azeotropic distillation of the formed water with suitable high boiling solvents such as toluene or xylene. Alternatively, the reactions may be effected in the presence of dehydrating agents such as molecular sieves or the like.

One of ordinary skill in the art, will appreciate that not all of the compounds of this invention may be readily prepared by any one process. However, it is clear that by selecting a particular process from those set forth above, all of the compounds of this invention may be prepared. Further, a number of the intermediates for preparing the compounds of this invention are commercially available or they may be readily prepared by art recognized methods. Intermediates for preparing a substantial number of the compounds of this invention are described or the preparation thereof is embodied in publications and treatises relating to peptide chemistry such as, J. H. Jones, in "Comprehensive Organic Chemistry", Vol. 2, D. Barton and W. D. Ollis, Editors, Pergamon Press, 1979 pp 819-823 and references 2, and 29-31 cited therein. The relevant portions of this publication are incorporated by reference herein.

In the following table, the shorthand notations $C_6H_5CH_2$ and $C_7H_7$ are both utilized to indicate the benzyl groups; $C_{10}H_7$ indicates the naphthyl group; $C_6H_5$ indicates the phenyl group; CbZ indicates the carbobenzoxy group; and $C_4H_3S$ indicates the thienyl group.

Utilizing the above described methods, the following compounds of the invention were prepared. All compounds have the L absolute stereochemistry at the chiral centers attached to $R_1$ and to $R_3$ equal to hydrogen. Absolute stereochemistry at the chiral center attached to $R_4$ is as indicated.

$R_1$—C*HCOR$_2$—NH—C*HR$_3$—CONH(CH$_2$)p—C*R$_4$R$_5$—COR$_6$

| Compound | R 1 | R 2 | R 3 | R 4 | R 6 | p | m.p. °C. | [α]D° (C. Solv.) |
|---|---|---|---|---|---|---|---|---|
| A | C$_6$H$_5$(CH$_2$)$_2$- | OH | C$_7$H$_7$— | CH$_3$(L) | OH | 0 | 176.9 | +12.0 (0.5, MeOH) |
| B | C$_6$H$_5$(CH$_2$)$_2$- | OH | 3-CH$_2$—C$_4$H$_3$S | CH$_3$(L) | OH | 0 | 192.5-3 | +4.0 (0.4, MeOH) |
| C | C$_6$H$_5$(CH$_2$)$_2$- | OH | 1-CH$_2$C$_{10}$H$_7$ | CH$_3$(L) | OH | 0 | 186-94 | — |
| D | (CH$_3$)$_2$CH— | OH | C$_7$H$_7$— | CH$_3$(L) | OH | 0 | 160-72 | — |
| E | Cbz—NH(CH$_2$)4- | OH | C$_7$H$_7$— | CH$_3$(L) | OH | 0 | 164-6 | — |
| F | C$_6$H$_5$CH$_2$SCH$_2$— | OH | C$_7$H$_7$— | CH$_3$(L) | OH | 0 | 152-4 | — |
| G | C$_6$H$_5$CH$_2$— | OH | (CH$_3$)$_2$CHCH$_2$— | C$_7$H$_7$(L) | OH | 0 | 178-80 | — |
| H | C$_6$H$_5$(CH$_2$)$_2$— | OH | C$_7$H$_7$— | H | OH | 1 | 202-4 | +8.1 (0.4, 0.1N NaOH) |
| J | C$_6$H$_5$(CH$_2$)$_2$— | OH | 1-CH$_2$C$_{10}$H$_7$ | H | OH | 1 | 206-7 | — |
| K | C$_6$H$_5$CH$_2$— | OH | C$_7$H$_7$— | H | OH | 1 | 222-3 | -28.4 (1.0, DMF) |
| L | C$_6$H$_5$CH$_2$— | —OCH$_2$C$_6$H$_5$ | C$_7$H$_7$— | H | —OCH$_2$OCOC(CH$_3$)$_3$ | 1 | oil | -25.0 (0.5, MeOH) |
| M | C$_6$H$_5$CH$_2$— | —OCH$_2$OCOC(CH$_3$)$_3$ | C$_7$H$_7$— | H | —OCH$_2$OCOC(CH$_3$)$_3$ | 1 | oil | -21.7 (1.0, DMF) |
| N | C$_6$H$_5$CH$_2$— | —OCH$_2$OCOC(CH$_3$)$_3$ | C$_7$H$_7$— | H | —OCH$_2$CH$_3$ | 1 | oil | -23.8 (1.0, DMF) |
| O | C$_6$H$_5$CH$_2$— | —OCH$_2$OCOC(CH$_3$)$_3$ | C$_7$H$_7$— | H | —OCH$_2$C$_6$H$_5$ | 1 | oil | -20.0 (1.0, DMF) |
| P | C$_6$H$_5$CH$_2$— | OH | C$_7$H$_7$— | H | —O(CH$_2$)$_2$O—C$_6$H$_5$ | 1 | 141-4 | -5.7 (0.4, MeOH) |
| Q | C$_6$H$_5$CH$_2$— | OH | C$_7$H$_7$— | H | —OCH$_2$OCOC(CH$_3$)$_3$ | 1 | 180-1 | — |
| R[a] | C$_6$H$_5$CH$_2$— | —OCH$_2$C$_6$H$_5$ | C$_7$H$_7$— | CH$_3$(R,S) | OH | 1 | 224-6 | — |
| S[a] | C$_6$H$_5$CH$_2$— | OH | C$_7$H$_7$— | CH$_3$(R,S) | —OCH$_2$OCOC(CH$_3$)$_3$ | 1 | oil | — |
| T[a] | C$_6$H$_5$CH$_2$— | OH | C$_7$H$_7$— | —CH$_2$C$_6$H$_5$(R,S) | OH | 1 | 235-7 | -23.7 (1.0, DMF) |
| U | 1-C$_{10}$H$_7$CH$_2$— | OH | C$_7$H$_7$— | H | OH | 1 | 185-7 | -27.8 (0.5, DME) |
| V | C$_6$H$_5$CH$_2$— | OH | 1-CH$_2$C$_{10}$H$_7$ | H | OH | 1 | 179-82 | -2.4 (0.5, MeOH) |
| W | p-CH$_3$C$_6$H$_4$CH$_2$— | OH | C$_7$H$_7$— | H | OH | 1 | 222-4 | -30.2 (0.5, DMF) |
| X | C$_6$H$_5$CH$_2$— | OH | p-C$_6$H$_5$—C$_6$H$_4$CH$_2$— | H | OH | 1 | 223-4 | -22.9 (0.5, DMF) |
| Y | 2-C$_{10}$H$_7$CH$_2$— | OH | C$_7$H$_7$— | H | OH | 1 | 220-2 | -8.6 (0.5, DMF) |
| Z | C$_6$H$_5$CH$_2$— | OH | 2-CH$_2$C$_{10}$H$_7$ | H | OH | 1 | 222-3 | -18.5 (0.5, DMF) |
| AA | p-ClC$_6$H$_4$CH$_2$— | OH | C$_7$H$_7$— | H | OH | 1 | 209-10 | -18.7 (0.5, DMF) |
| AB | p-CH$_3$C$_6$H$_4$CH$_2$— | OH | C$_7$H$_7$— | H | OH | 1 | 193-4 | -26.7 (0.5, DMF) |
| AC | p-C$_6$H$_5$—C$_6$H$_4$CH$_2$— | OH | C$_7$H$_7$— | H | OH | 1 | 226-8 | -16.8 (0.5, DMF) |
| AD | C$_6$H$_5$CH$_2$— | OH | p-C$_6$H$_5$—C$_6$H$_4$CH$_2$— | H | —OCH$_2$OCOC(CH$_3$)$_3$ | 1 | 229-30 | -7.5 (0.5, DMF) |
| AE | C$_6$H$_5$CH$_2$— | OH | C$_7$H$_7$— | H | OH | 2 | amorphous | — |
| AF | C$_6$H$_5$CH$_2$— | —NHC$_6$H$_4$-o-CH$_3$ | C$_7$H$_7$— | H | OH | 0 | 191-92 | — |
| AG[b] | C$_6$H$_5$CH$_2$— | OH | (CH$_3$)$_2$CHCH$_2$— | C$_7$H$_7$(L) | OH | 1 | 207-9 | -18.4 (1.0, DMF) |
| AH | C$_6$H$_5$CH$_2$— | OH | C$_6$H$_5$CH$_2$— | OH(S) | OH | 1 | 210-11 | -17.9 (1.0, DMF) |
| AI | C$_6$H$_5$CH$_2$— | OH | C$_6$H$_5$CH$_2$— | OH(R) | OH | 1 | 209-11 | -34.0 (1.0, DMF) |
| AJ | C$_6$H$_5$CH$_2$— | OH | C$_6$H$_5$CH$_2$— | OCH$_3$(S) | OH | 1 | 209-11 | +26.0 (1.0, DMF) |
| AK | C$_6$H$_5$CH$_2$— | OH | C$_6$H$_5$CH$_2$— | OCH$_3$(R) | OH | 1 | 180-2° | — |
| AL | C$_6$H$_5$CH$_2$— | OH | C$_6$H$_5$CH$_2$— | NHCO$_2$t-C$_4$H$_9$(S) | OH | 1 | | |

[a] 1:1 mixture of D & L diastereomers
[b] D stereochemistry at chiral center bonded to $R_1$ As used herein, unless stated otherwise, the terms alkyl and alkoxy denote such groups having straight or branched carbon chains of from 1 to 6 carbon atoms. The term pivaloyloxymethyl is the trivial or common name for the (2,2-dimethyl-1-oxopropoxy)methyl group.

Halogen includes fluorine, chlorine, bromine and iodine.

Certain of the compounds having structural formula I form salts with pharmaceutically acceptable acids. Hydrochloric, sulfuric, acetic, maleic, fumaric and the like may be utilized.

Compounds having structural formula I wherein $R_2$ and/or $R_6$ are hydroxy form salts with pharmaceutically acceptable bases. Sodium, potassium and calcium hydroxide as well as sodium and potassium carbonate are examples of suitable bases for this purpose. In addition, salts formed with pharmaceutically acceptable amines such as, for example, ammonia, N-methylglucamine, benzylamine and morpholine are also contemplated.

In formula I, the asterisks denote those carbon atoms which may be asymmetric (chiral) centers. The invention contemplates all isomers at these centers both in pure form and in admixture.

The preferred stereochemistry at the chiral centers to which the $R_1$ and $R_3$ substituents are attached is that configuration most similar to that of the natural L-amino acids. Usually, natural L-amino acids are assigned the S- configuration by convention. A notable exception is the natural amino acid L-cysteine which is assigned the R- configuration by convention.

The compounds having structural formula I inhibit the activity of enzymes designated enkephalinases. The compounds are particularly useful for the inhibition of enkephalinase A, which is derived from the striata of both rats and humans. In in vitro tests, selected compounds having structural formula I in a concentration range from 10-9 to 10-6M have been found to inhibit the activity of the aforementioned enzyme by 50% or more.

The following test procedure was utilized to assay the enkephalinase A inhibition of the compounds having structural formula I.

Enkephalin (ENK) degrading activity was separated into the following three fractions according to the method of Gorenstein and Snyder, Life Sci., 25, 2065 (1979) : Enk'ase A (Gly$^3$-Phe$^4$), Aminopeptidase, (AP) (Tyr$^1$-Gly$^2$), and Enk'ase B (Gly$^2$-Gly$^3$).

Enzyme activity was separated by taking the brain tissue (minus cerebellum) from Sprague-Dawley rats and homogenizing it in 30 volumes of 50 mM Tris buffer, pH 7.4, using a Brinkmann Polytron. The resulting homogenate is centrifuged at 50,000×g for 15 min. The pellet, constituting the membrane bound enzyme xaterial, is washed by resuspending it in Tris and re-centrifuging it 4 times.

Following washing, solubilization of the membrane pellet is achieved by incubating it for 45 min at 37° C. in the presence of 15 volumes (based on initial brain weight) of 50 mM Tris-1% Triton X-100 buffer, pH 7.4. After centrifugation at 100,000×g for 60 minutes to remove non-solubilized material, the Triton soluble supernatant is layered on a 1.5×30 cm DEAE Sephacel column previously equilibrated with 50 mM Tris-0.1% Triton, pH 7.4. Material is eluted from the column using a 1 liter linear NaCl gradient running from 0.0 to 0.4M. Effluent is collected in 7 ml fractions, each of which is assayed for enkephalin degrading activity. Under these conditions Enk'ase A activity is found to elute between 120 and 200 ml. followed by AP activity (260 to 400 ml) and finally by Enk'ase B activity between 420 and 450 ml.

Enkephalin degrading activity is monitored using a radiometric assay. The substrate is $^3$H-Met$^5$-ENK (50.1 Ci/mmol, New England Nuclear) diluted in 0.05M Tris buffer, pH 7.4, such that the final reaction mixture concentration is 40 nM. Total reaction mixture volume including enzyme and substrate is 250 μl. Incubation is carried out for 90 min at 37° C. To stop the reaction, tubes are transferred to a boiling water bath for 15 min.

Assay products are separated from one another using thin layer chromatography A 4 μl aliquot of the reaction mixture is spotted on a Baker-flex Silia Gel 1B plate (20×20 cm) along with unlabeled standards (Met$^5$-ENK, tyrosine, tyrosyl-glycine, tyrosyl-glycyl-glycine) and the components co-chromato-graphed in an iso-propanyl:ethyl acetate: 5% acetic acid solvent system (2:2:1) which is capable of resolving Met$^5$-ENK from its breakdown products. Total running time is approximately 17 hours. TLC tanks are gassed with nitrogen prior to starting the run. Following the run, markers are visualized with ninhydrin spray. These spots, along with remaining plate regions, are cut from the plate and the radioactivity corresponding to each monitored using liquid scintillation counting. IC$_{50}$'s are determined using linear regression techniques.

Utilizing this procedure, the following nanomolar (nM) concentrations for the specified compounds were found to inhibit the action of enkephalinase A by 50% (IC$_{50}$).

TABLE A

| Compound | Enkephalinase A Inhibition IC$_{50}$nM |
|---|---|
| A | 90 |
| B | 140 |
| C | 30 |
| D | 1340 |
| E | 220 |
| F | 170 |
| G | 140 |
| H | 15 |
| J | 15 |
| K | 15 |
| L | N.A.$^1$ |
| M | N.A.$^1$ |
| N | N.A.$^1$ |
| O | N.A.$^1$ |
| P | 230 |
| Q | 580 |
| R | 6.4 |
| S | N.A.$^1$ |
| T | 6.3 |
| U | 5.0 |
| V | 90 |
| W | 7.5 |
| X | 15 |
| Y | 46 |
| Z | 16 |

| Compound | Enkephalinase A Inhibition IC$_5$ nM |
|---|---|
| AA | 22 |
| AB | 29 |
| AC | 2.5 |
| AD | 0.9 |
| AE | 55 |
| AF | N.A.$^1$ |
| AG | 12 |
| AH | 11 |
| AI | 15 |
| AJ | 17 |
| AK | 52 |

TABLE A-continued

| | |
|---|---|
| AL | 4.5 |

[1] No activity at $< 10^5$ nM

The following test procedure was utilized to assess the noted compounds' potentiation of the analgesic effects of (DAla$^2$-Met$^5$)-enkephalinamide (DAEAM). Background for the use of this procedure is given in Chipkin, R. E., Iorio, L. C., Barnett, A., Berger, J., and Billard, W., *Regulatory Peptides: From Molecular Biology to Function*, edited by E. Costa and M. Trabucchi, Raven Press, New York, 1982, pp. 235–242.

Male CF1 mice (19–23 g) from Charles River Breeding Labs, Mass., are used (N=10/dose or dose combination). Tail-flick testing is done similar to that of Dewey and Harris, *Methods in Narcotic Research*, Eds., S. Ehrenpreis and A. Neidle, pp. 101–109, Marcel Dekker, Inc., New York, 1975 using a radiant heat noxious stimulus. Following determination of control latencies (typically 2–3 sec), the mice are first injected (sc or po) with either vehicle or drug and after an appropriate interval injected intracerebroventricularly (icv) with either vehicle (10 ul of saline) or DAEAM according to Haley and McCormick, *Br., J. Pharmacol.*, 12,12 (1957). Tail-flick latencies are re-determined 30 min later, as this has previously been determined to be the time of peak analgesia for DAEAM, a cut-off of 10 sec is employed.

Utilizing this procedure, the following ED50 values (the dose at which half the test animals displayed analgesia) were obtained for selected compounds.

TABLE B

| Compound | DAEAM Potentiation ED$_{50}$ (route) |
|---|---|
| K | 17 mg/k (sc) |
| L | 155 mg/k (po) |
| M | 37 mg/k (po) |
| N | 100 mg/k (po) |
| O | 100 mg/k (po) |
| P | 30–60 mg/k (po) |
| Q | 100 mg/k (sc)$^2$ |
| R | 50 ug (icv) |
| S | 100 mg/k (po) |
| T | 50 ug (icv)$^2$ |
| AB | 10 mg/k (sc) |
| AD | 50 ug (icv)$^2$ |
| AF | 100 mg/k (po) |

[2] ED100

It should be noted that compounds L, M, N and O are ester derivatives of compound K, compound S is an ester derivative of compound R and compound AF is an amide derivative of compound K. Such derivatization is employed to confer oral activity to the parent entity because of the poor absorption properties of these compounds from the gastrointestinal tract. These derivatives, which show no activity in vitro at $< 10^5$ nM (see table A), are bioactivated in vivo to deliver the parent (in vivo enkephalinase A inhibitors) to a site of action within the central nervous system (see table B).

The compounds of the invention may also be used in the treatment of mental disorders such as depression and schizophrenia by administering an antidepressant or antipsychotic effective amount of such a compound to a mammal in need of such treatment. For example, the antidepressive characteristics of the compounds of formula I may be demonstrated by the Porsolt behavioral despair test in mice (Posolt et al., *Arch. Int. Pharmacodyn. Ther.*, 229: 327–336 (1977).

MATERIALS AND METHODS

Mail CD1 mice weighing between 26 and 30 g were used. Animals were allowed to acclimate to the laboratory for one hour prior to subcutaneous (sc) or intraperitoneal (ip) injection with either vehicle or drug at a volume of 10 ml/kg body weight. Thirty minutes or one hour following injection, mice were placed in a circular tank (diamter=14.5 cm) filled with water (temperature 20°±1° C.) to a depth of 11 cm. Duration of immobility, defined as the absence of all body movement, was timed for the last 4 minutes of the 6 minute test period. All experiments were done using 8 animals per group in a counter-balanced design. Data are expressed as the mean (±SE) for each test group in seconds. All drug doses are expressed as the free base.

RESULTS

Animals treated with vehicle showed substantial immobility when forced to swim in an inescapable situation. This was reversed by desipramine (30 mg/kg ip). Likewise, the amount of immobility ovserved was also decreased by administration of N-[N-[(L)-[1-(2,2-dimethyl-1,3-dioxan-4-yl)-methoxy]carbonyl]phenylethyl]-L-phenylalanyl]-β-alanine (Compound AM) in a dose-related manner (see Table C below). These data indicate that Compound AM has antidepressant-like activity. These results agree with Natan et al. (*EJP*, 97:301–304 (1984) showing a similar effect of another enkephalinase inhibitor (thiorphan) in this test.

TABLE C

Effect of Vehicle, Compound AM or Desipramine in the Mouse Behavioral Despair Test

| Treatment | Dose (mg/kg) | N | Mean (±SE) Immobility Time (in Sec) Post-Treatment |
|---|---|---|---|
| Vehicle | — | 8 | 159.9 ± 7.0 |
| Compound AM$^a$ | 30 sc | 8 | 129.8 ± 13.1 |
| | 100 sc | 8 | 50.0 ± 10.3* |
| Desipramine$^b$ | 30 ip | 6 | 40.2 ± 9.3* |

[a] Compound AM as tested 30 minutes post-treatment.
[b] DMI was tested 60 minutes post-treatment.
*Sig. difference from vehicle $P < .05$, Student's t-test.

The compounds having structural formula I may be utilized to exert their analgesic or antidepressive effect in the many dosage forms known to the art, such as tablets, capsules or elixirs for oral administration or in sterile solutions or suspensions for parenteral administration. The foregoing pharmaceutical dosage forms are advantageously prepared using, in addition to a compound of this invention, pharmaceutically acceptable and compatible excipients, binders, preservatives, stabilizers, flavors and the like. In each of the dosage forms the active compound will be administered in a dosage in the range of from about 1 to about 100 m.p.k. The doses are to be administered at intervals of from 3 to 8 hours. However, the quantity and frequency of dosage will depend upon such factors as the severity of the pain, the general physical condition of the patient, including the age and weight of the patient and other factors which a person skilled in the art will recognize.

The following examples illustrate the preparation of the compounds of the invention.

EXAMPLE 1

N-[N-[L-1-Carboxy-2-(4-phenyl)phenylethyl]-L-phenylalanyl]-β-alanine benzyl ester

A. 4-Phenylphenylpyruvic Acid 40 g of Potassium t-butoxide was added to 150 ml of diethyl oxalate in small portions with stirring. After the initial exothermic reaction subsided, the reaction mixture was heated on a steam bath under nitrogen in order to dissolve solids. After cooling down to room temperature, 79 g of 4-biphenyl acetic acid methyl ester was added in one portion. The mixture was stirred at 60°–70° C. for 2 hours while low boiling material was removed under vaccum. On cooling to room temperature, the viscous residue was stirred with 200 ml of ether and 350 ml of water with cooling. The ether layer was separated and extracted once with 100 ml of water. The aqueous layers were combined, extracted once with ether, made acidic with concentrated HCl (cooling) and extracted with 2×300 ml of ether. Some solids did not dissolve in the ether layer and were filtered. The ether layer was then evaporated to dryness. and the semi solid residue was combined with the preceeding solids. A mixture of 160 ml of conc. HCl and 350 ml of acetic acid was added to the solids and heated under reflux for 2½ hours. On cooling down to ca. 50° C. a solid preciptated, which was filtered and washed with 150 ml of water. The wet solid was stirred with 150 ml of acetonitrile for five minutes, then filtered and dried under high vaccum at room temperature for 3 hours. 42.2 g of the title compound m.p. 215°–218° C. were obtained.

B. N-[N-[N-tert.-butyloxycarbonyl]-L-phenylalanyl]-β-alanine benzyl ester

To a stirred mixture of 0.023 mole each of di-t-butyl-dicarbonate, L-phenylalanine, β-alanine benzyl ester p-toluenesulfonate, hydroxybenzotriazole, N-dimethylamino propyl-N'-ethylcarbodiimide hydrochloride in 75 ml of dry N,N-dimethylformamide in an ice bath was added 5 ml of N-ethyl-morpholine. Stir at room temperature for 3 hours. Pour into 600 ml of ice water and extract with 3×150 ml of ether. Et$_2$O layers were combined and extracted once with 150 ml of 0.3N HCl. Et$_2$O layer is extracted twice with 300 ml of water. Et$_2$O layer is dried over Na$_2$SO$_4$, filtered and evaporated down to dryness at 28° C. in vacuo. Obtain 9.0 g of gummy solid residue.

C. N-(L-Phenylanyl)-β-alanine benzyl ester hydrochloride 4.0 g of the xaterial from example 1B in 25 ml of ethyl acetate at 0° C. was stirred with gaseous HCl for 10 min Stir at 0° C. for 1½ hours then at 10<C. for 30 min. A stream of N$_2$ was passed into the solvent to expel excess HCl. The solution was poured into 200 ml of ether with vigorous stirring, and the precipitated solid filtered. Dry at room temperature under high vacuum for 2 hours to give 3.35 g. of product.

D. N-[N-[L-1-Carboxy-2-(4-phenyl)phenylethyl]-L-phenylalanyl]-β-alanine benzyl ester A mixture of 9.10 g of N-(L-phenylalanyl)-β-alanine benzyl ester hydrochloride and 8.40 g of the compound of example 1A in 500 ml of a mixture of tetrahydrofuran-ether (9:1) was treated with triethylamine to pH 6.6 and stirred at room temperature for 1½ hours. A solution of 2.0 g of sodium cyanoborohydride in a mixture of 100 ml of tetrahydrofuran-ethanol was added dropwise over a period of 2 hours with stirring. Stirring was continued at room temperature overnight. The reaction mixture was concentrated to ca. 75 ml. at 40° C. in vacuo. The residue was stirred with 400 ml each of 0.5N HCl and ether for one hour. The ether layer was dried over sodium sulfate, filtered and evaporated to dryness in vacuo. A yellow viscous syrup was obtained which was dissolved in 25 ml of ethanol. Solids were formed on refrigeration over night which were filtered off and washed with cold ethanol (4.2 g). This material was applied to a column of 300 g of silica gel in a solvent mixture consisting of CHCl$_3$:CH$_3$OH:CH$_3$CO$_2$H (200:10:2) and material eluted with the same solvent. The effluent was divided into fractions which were evaporated to dryness in vacuo. In this xanner, 600 mg of a solid product consisting of the title compound, m.p. 192°–4°, were obtained.

EXAMPLE 2

N-[N-[L-1-Carboxy-2-(4-phenyl)phenylethyl]-L-phenylalanyl]-β-alanine

A suspension of 590 mg of the product from example 1 in 100 ml of ethanol was shaken overnight with 200 mg of 10% Pd/C in a Parr apparatus. The resulting mixture was diluted with 40 ml of ethanol and 10 ml of water then heated on a steam bath briefly until all white precipitate dissolved. After cooling, the catalyst was filtered off. The filtrate was evaporated at 50° C. under vacuum to ca. 5 ml. The solid was filtered, washed with ethanol, and dried at room temperature under high vacuum for 6 hours to yield 155 mg of the title compound m.p. 226°–228° C. $[\alpha]D^{26} = 16.8$ (C=0.5, DMF). Analysis Calc'd: C, 70.40; H, 6.13; N, 6.08. Found: C, 70.54; H, 6.26; N, 5.97.

EXAMPLE 3

N-[N-[L-[1-[Pivaloyloxymethoxy]carbonyl]-2-phenylethyl)]-L-phenylalanyl]-β-alanine, pivaloyloxymethyl ester

A. N-(tert.-Butyloxycarbonyl)-β-alanine, pivaloyloxymethyl ester

Triethylamine (32.4 ml) was added to N-tert.-butyloxycarbonyl β-alanine (40 g) in N,N'-dimethylformamide at room temperature under a nitrogen atmosphere in a 1 l round bottom flask. The solution was stirred 15 minutes and chloromethyl pivalate (36.6 g) [M. Rasmussen & N. J. Leonard, J. Amer. Chem. Soc., 89, 5439 (1967)] was added dropwise at 0° C. The solution was stirred at room temperature overnight. The mixture was then diluted with ethyl acetate, filtered, washed with water, then brine, and evaporated to give 70 g crude material which was chromatographed (silica gel) eluting with 15% ethyl acetate-hexane to give 62.5 g of product.

B. β-Alanine, pivaloyloxymethyl ester, trifluoroacetate

Trifluoroacetic acid (100 ml) was added to a solution of the product from example 3A (62 g) in methylene chloride (180 ml) at 0° C. The mixture was stirred at room temperate for two hours, and solvent removed in vacuum to give 100 g product as a pale yellow oil.

C. N-[L-1-(Phenylmethoxy)carbonyl-2-phenylethyl)]-L-phenylalanine

L-Phenylalanine benzyl ester hydrochloride, 190.4 g (0.652 mole) is suspended in 960 mls abs. methanol, 6.7 l dry (3A sieves) tetrahydrofuran added and the slurry is stirred while adding triethylamine to pH 6.5–7.0 (about 50 ml is required). The pH is checked with EM Reagents ColorpHast indicator sticks, range pH 5–10, moistened with water before use. To the neutral slurry is added 200 g (0.98 mole) sodium phenyl pyruvate hydrate (Sigma), followed by 240 g crushed 3A molecular sieves. (Sieves may be ground in a mortar and need not be finely powdered. If too fine, they are difficult to remove by filtration). The slurry is stirred at ambient temperature while adding a solution of 61.6 g (0.98 mole) sodium cyanoborohydride in 40 ml methanol plus 300 ml dry tetrahydrofuran dropwise over 5 hours. The reaction is stirred at ambient temperature for 48 to 72 hours while monitoring the disappearance of Phe benzyl ester by t.l.c. The reaction mixture is filtered to remove sieves, washing sieves well with hot methanol, as some product precipitates out on them. The filtrate is concentrated on a rotary evaporator at 50° C. to a syrup. This syrup is dissolved in 2.4 l ether in a 12 l round bottomed flask and stirred in an ice bath while adding 2.4 l 2.5% HCl (aqueous). The large volume of HCN which is generated is passed into a sodium hydroxide trap. The mixture is allowed to stir for 2.5 to 3 hours while a white solid gradually forms at the interface and evolution of HCN stops. The 2-phase mixture is filtered (most of the aqueous may be drawn off in a separator before filtering as product remains at the interface) and the solid is washed well with ether and dried in vacuo below 50° C., wt 80–90 g, m.p. 175°–180° C. This material is 90–95% pure L,L isomer by t.l.c. estimate. The crude product is redissolved in about 10 l boiling abs. methanol, some fine white inorganic insolubles filtered and the filtrate conc. to ca 5 l at the boiling point, when flocculent white crystals appear. The product is allowed to cool slowly to room temperature and then to 0° C. for 2–3 hours. The solid is collected and dried in vacuo at 50°, wt 57–60 g, m.p. 185°–186° C., [α]D26 5.9 to 6.3° C.* (DMSO, C=1). The product is greater than 98% L,L isomer by t.l.c. and HP analysis.
*(results of several runs)

D. N-(L-1-Benzyloxycarboyl-2-phenylethyl)-L-phenylalanine pivaloyloxymethyl ester A solution of 4.03 g (10 m mole) of the product from example 3C and 1.5 ml (11 mmole) triethylamine in 20 ml DMF was treated at ambient temperature with 1.6 ml (11 mmole) of chloromethyl pivalate. Stirred at 50–60<C. for 24 hours. Poured the slurry into water and extracted with 3×100 ml ether. Filtered some insolubles, washed ether phase with water, dried and conc to an oil, 4.8 g., NMR consistent with structure.

E. N-(L-1-Carboxy-2-phenylethyl)-L-phenylalanine, pivaloyloxy-methyl ester

The crude diester from example 3D (4.8 g) was hydrogenated on Parr apparatus at 60 psig in 50 ml methanol +5 ml $H_2O$ over 0.4 g 10% Pd C for 3 hours. Filtered and concentrate to a damp solid which was recrystallized from methanol/$H_2O$. Filtered white fluffy needles and dried in vacuo, wt 3.0 , m.p. 122°–124° C.

TLC showed essentially one spot, $R_f$ 0.2 in $CHCl_3$/MeOH/HOAc 100:1:0.0.5.

F. N-(L-1-Pivaloyloxymethylcarbonyl-2-phenylethyl)-L-phenyl-alanine, pivaloyloxymethyl ester A mixture of 1.0 g (2.3 mmole) of the product from Example 3E and 0.89 g (2.3 mmole) of the product from example 3B in 25 ml DMF was treated with 1.01 ml (8 mmole) N-ethyl-morpholine followed by 352 mg (2.3 mmole) 1-hydroxybenzotriazole hydrate and 439 mg (2.3 mmole) 1-(3-dimethylaminopropyl)-3-ethyl carbodiimide hydrochloride, and allowed to stir at ambient temperature overnight. Thin layer chromatography still showed starting material present. The reaction mixture was heated to 40°–50° C. for 6 hours and allowed to stand at room temperature overnight. The mixture was poured into water and extracted with several portions of ether, the ether phase washed well with water, dried and concentrated to an oil (1.2 g). The oil was chromatographed on Merck t.l.c. grade silica gel 60-G to yield 0.9 g oil showing a single spot, Rf 0.4 in EtOAc/Hexane 1:2 (same system as used for column chromatography.) Anal. Calculated for C33H44N2O9: C, 64.69; H, 7.24; N, 4.57. Found: C,64.47; H,7.20; N,4.29 $[\alpha]D^{26}$ −21.7° (DMF, c=1.0).

EXAMPLE 4

N-(L-1-Benzyloxycarbonyl-2-phenylethyl)-L-phenylalanyl-β-alanine, benzyl ester

The product from example 3C (16 g, 39.7 mmole), β-alanine benzyl ester tosylate (13.9 g, 39.7 mmole), 1-hydroxybenzotriazole hydrate (6.07 g, 1 equiv.), N-ethylmorpholine (14.8 ml, 3 equiv.) and 250 ml dry DMF were stirred at room temperature. Added 1 equiv. (7.58 g) of 1-(3-dimethyl-aminopropyl)-3-ethyl carbodiimide hydrochloride. The clear solution was allowed to stir overnight. The resulting dark yellow solution was poured into ca. 600 ml cold water and extracted with 3×300 ml ether. The ether solution was washed repeatedly with water, dried and concentrated to an oil, (21 g). NMR consistent with product. TLC shows a single spot, $R_f$ 0.7 ($CHCl_3/CH_3OH$/AcOH - 100:5:0.5).

EXAMPLE 5

N-(L-1-Carboxy-2-phenylethyl)-L-phenylalanyl-β-alanine

The crude dibenzyl ester (21 g) from example 4 was dissolved in 200 ml MeOH plus 10 ml water and hydrogenated at 60 psig. over 1 g 10% Pd/c for 4 hours. By the end of this time, the product had precipitated out in the reaction bottle. The hydrogenation mixture was diluted to ca. 500 ml with methanol and heated to boiling. Addition of ca. 20 ml pyridine brought all solid into solution. Filtration thru celite and diatomaceous earth and concentration on a rotary evaporator at 80° C. gave 13.3 g of white solid after drying in high vac. (93%). This solid was dissolved in 250 ml water containing 50 ml 1N NaOH. The basic solution was extracted with a few ml ether and filtered thru celite and diatomaceous earth. The basic solution was then acidified to pH 3.4 with 10% HCl. After cooling 2 hours the precipitated solid was collected by filtration. Dried at 50° C. in vacuo overnight to yield 13.2 g product, $[\alpha]D^{26}$−28.4° (DMF, c=1.0). Anal. Calculated for C21H24N2O5: C, 65.61; H,6.29; N, 7.28. Found: C,64.85; H,6.28; N, 7.20.

EXAMPLE 6

N-[N-[L-[1-[(2,2-Dimethyl-1-oxopropoxy)methoxy carbonyl]-2-(4-phenyl)-phenylethyl]-L-phenylalanyl]-β-alanine

A.
N-D,L-1-Carboxy-2-(4-phenyl)phenylethyl]-L-phenylalanine, benzyl ester

A stirred suspension of 4-phenylphenylpyruvic acid (24.0 g) and L-phenylalanine benzyl ester hydrochloride (23.2 g) in 1 l. of THF/ethanol (9:1) was brought to pH 6.6 by gradual addition of triethylamine. In the course of this process, all solids dissolved. After stirring the resulting solution for 2 hours at room temperature, a solution of sodium cyanoborohydride (3.5 g) in the same solvent was added dropwise with stirring. The reaction mixture was allowed to stir overnight at room temperature.

The reaction mixture was then concentrated to 200 ml under reduced pressure. The residue was poured into 600 ml of 0.3N HCl with cooling and stirring. A gummy solid separated. The acueous material was decanted off, and the remaining solid stirred with 120 ml of ethanol. The resulting solids were filtered, and the wet solids stirred with 100 ml of fresh ethanol. After standing overnight, the solids were filtered and dried to give 22.3 g of solid product.

B.
N-[D,L-[1-[(2,2-Dimethyl-1-oxypropoxy)-methoxy]-carbonyl]-2-(4-phenyl)phenylethyl]-L-phenylalanine, benzyl ester Triethylamine (3.05 ml.) was added to a solution of N-[D,L-1-carboxy-2-(4-phenyl)phenylethyl]-L-phenylalanine, benzyl ester (9.6 g) in 30 ml of dimethylformamide. The mixture was stirred at room temperature for 20 min. and chloromethyl pivalate (3.15 ml) was added. The resulting mixture was heated in a bath at 45°-55° C. for 4 hours with stirring, then allowed to stir at room temperature overnight. The resulting mixture was diluted with 300 ml of water and extracted with three 150 ml portions of ether. The combined ether layers were extracted with 2-100 ml portions of water, and the ether solution dried over anhydrous Na2SO4. Filtration and evaporation in vacuo gave 7.5 g of syrupy product.

This material was chromatographed on 135 g of silica gel eluting with a mixture of ethylacetate cyclohexane (85:15). Fractions containing the desired diasteromeric mixture of products were identified by thin-layer chromatography, combined, and evaporated to dryness in vacuo to give 5.9 g of product as a syrup.

C.
N-[D,L-[1-[(2,2-Dimethyl-1-oxopropoxy)methoxy]carbonyl]-2-(4-phenyl)phenylethyl]-L-phenylalanine A solution of the above product (5.9 g) in 175 ml. of ethanol was hydrogenated at 15-30 psig over 750 mg. of 10% Pd/C for 2 hours. The reaction mixture was diluted with an additional 250 ml. of ethanol and warmed to 45° to dissolve the precipitated product. Catalyst was filtered from the warm solution, and the filtrate evaporated to give a total of 4.4 g product.

D. N-[N-[L-[1-[(2,2-Dimethyl-1-oxopropoxy)methoxy carbonyl]-2-(4-phenyl)phenylethyl]-L-phenylalanyl]-β-alanine, benzyl ester N-ethylmorpholine (1.2 ml) was added to a stirred mixture of the above product (3.25 g), N-(N,N-dimethylaminopropyl)-N'-ethylcarbodiimide hydrochloride (1.7 g), hydroxy-benzotriazole (1.3 g) and α-alanine benzyl ester p- toluenesulfonate (3.0 g) in 25 ml of dimethylformamide. The mixture was stirred at room temperature for 3 hours, diluted with 200 ml of ice-water and extracted with two 125 ml portions of ether. The combined extracts were washed with 250 ml of water and dried over anhydrous MgSO4. Filtration and evaporation gave 5.25 g of residue. Thin-layer chromotography (silica gel, CHCl3/EtOAc - 10:1) showed two major products, $R_f=0.36$ and $Rf=0.32$ (partially overlapping). This xaterial was chromatographed on 350 g of silica gel (thin-layer chromotography grade), eluting with CHCl3-EtOAC (100:5). Fractions containing the pure individual components were identified by thin-layer chromatography, combined and evaporated. In this manner, 650 mg of faster moving component (L,L-diasteromer) was obtained along with 590 mg of L,D-diasteromer.

The final product was obtained by hydrogenating a solution of 650 mg of L,L-diasteromer above in 50 ml ethanol over 50 mg of 10% Pd/C at 15-45 psig for 3 hours. Catalyst was filtered off, and the filtrate evaporated to dryness in vacuo at 30° C. The residue was chromatographed on 50 g of t.l.c. grade silicagel, eluting initally with 300 ml of CHCl3/EtOAC (10:1), then with CHCl3/CH3OH/AcOH (600:10:2). Fractions containing pure product were identified by thinlayer chromatography (silicagel) CHCl3/CH3OH/AcOH (600:10:2), $R_f=0.31$. These fractions were combined, evaporated, and the residue dried at room temperature in high vacuum overnight. The residue was recrystalized from either and the product dried at 45° C. for 3½ hours in high vacuum. Obtain 250 mg. solid, m.p. 101°-103° C., $[\alpha]D^{26}-22°$ (c=0.5, DMF).

EXAMPLE 7

N-[N-[L-[1-(2,2-Dimethyl-1-oxyproxy)methoxy]carbonyl]-2-phenylethyl]-L-phenylalanyl]-β-alanine A mixture of 0.9 g (2.1 mmole) of N-(L-1-carboxy-2-phenylethyl)-L-phenylalanine, pivaloyloxymethyl ester (Example 3E) and equimolar amounts of β-alanine benzyl ester p-toluenesulfonate (737 mg), 1-hydroxybenzotriazole hydrate (321 mg) and 1-(3-dimethylaminopropyl)-3-ethyl-carbodiimide HCl (401 mg) were dissolved in 20 ml DMF containing 0.8 ml (6.3 mmole) N-ethylmorpholine and the mixture allowed to stir at ambient temperature overnight.

The yellow solution was poured into water (ca. 150 ml) and extracted with 3×100 ml ether. The ether phase was washed with water, dried and concentrated to an oil, 1.1 g showing one major spot with minor impurity on thin-layer chromatography.

The total was chromatographed on ca. 150 g silica gel eluting with ethyl acetate/hexane (30:70). The fractions were combined and concentrated to an oil, $[\alpha]D26-20.0°$ (DMF, c=1).

The above-described product (1.5 g) was hydrogenated at 40 psig in 100 ml abs. EtOH over 0.2 g 10% Pd/C for 3 hours.

Catalyst was filtered and the filtrate concentrated to an oil which crystallized upon drying in high vacuum overnight. On standing under hexane fine colorless crystals were obtained, which on filtration and drying gave 1.2 g of product, m.p. 93°-95° C., $[\alpha]D^{26}-27.3°$ (DMF, c=1).

EXAMPLE 8

N-[N-(L-1-carboxy-2-phenylethyl)-L-phenylalanyl]-S-2-[N-[(1,1-dimethylethoxy)carbonyl]amino]-β-alanine

A. (L)-3-amino-2-(N-(t-butyloxy)carbonyl)propionic acid, ethyl ester succinate (L)-3-(N-benzyloxy)carbonyl)-2-aminopropionic acid, ethyl ester hydrochloride (3.09, 9.9 mmole, prepared in accord with Bull Chem. Soc. Japan 54, 297 (1981) and triethylamine (1.4 ml, 10 mmol) were dissolved in 10 ml. of tetrahydrofuran and treated with di-t-butyldicarbonate (Fluka, 2.2 g. 10 mmol) in several ml. of tetrahydrofuran. The mixture was stirred at room temperature for 4 hrs., salts filtered and the filtrate concentrated to an oil which was dissolved in 30 ml of ether. The resulting solution was washed with 10 ml of water, dried, and concentrated to an oil (4 g.)

This material was dissolved in 50 ml of absolute ethanol, a solution of succinic acid (1.18 g, 10 mmol) in ethanol added and the resulting solution hydrogenated in a Parr apparatus over 0.3 g of 10% Pd/C at 60 psig for 3 hrs. Catalyst was filtered off and the filtrate concentrated to a white solid which was triturated with ether to yield 2.5 g of crystrals. Recrystallization from ethyl acetate gave 1.9 g., m.p. 100°-101° C., $[\alpha]D^{26} - 20.1°$ (c=1, DMF).

B. N-[N-(S)-1-carboxy-2-phenylethyl)-(L)-phenylalanyl]-(L)-2-[[(2,2-dimethylethoxy)carbonyl]amino]-β-alanine A mixture of the product of example 3C (2.0 g, 4.96 mmol), the product from part A above (1.89 g, 5 mmol), 1-(3-dimethylaminopropyl)-3-ethyl carbodimide hydrochloride (0.958 g, 5 mmol) and 10 ml. of dimethylformamide was treated with 1.9 ml (15 mmol) of N-ethylmorpholine and the resulting mixture stirred at ambient temperature overnight. At the end of this time, an additional 500 mg of the carbodiimide and 0.5 ml N-ethylmorpholine were added and the mixture stirred an additional 24 hrs. The reaction mixture was then poured into ice-water, and admixed with ether. Some solids separated which were filtered off. The 2 phase filtrate was shaken with 200 ml of ethyl acetate, the organic layer separated, washed well with water, dried, and concentrated to an oil (2.0 g). This material was chromatographed on 150 g of silica gel eluting with ethyl acetate/hexane 2:3. The purified product was thus obtained (1.2 g) as an oil which slowly crystallized on standing.

This product (0.4 g) was dissolved in 5 ml of acetonitrile and treated with 2 ml of 1N NaOH at room temperature overnight. Solvents were evaporated in vacuo, and 5 ml. each of water and ether added to the residue. The ether layer was separated and discarded. The aqueous phase was neutralized to pH6 and extracted with ethyl acetate. Dilution of this dried extract with hexane gave 65 mg of final product, m.p. 180°-182° C. dec.

EXAMPLE 9

N-[N-[(L)-[1-(R,S)-(2,2-dimethyl-1,3-dioxolan-4-yl)-methoxy]-carbonyl]-2-phenylethyl]-(L)-phenylalanyl]-(R)-2-hydroxy-β-alanine

A. (L)-N-(1-benzyloxycarbonyl-2-phenylethyl)-(L)-phenylalanine, cyanomethyl ester A solution of the product of example 3C (4.03 g, 10 mmol) and triethylamine (2.1 ml, 15 mmol) in 150 ml acetone was treated dropwise at room temperature with 0.95 ml (15 mmol) of chloroacetonitrile. The resulting mixture was heated at reflux overnight. The reaction mixture was then concentrated to dryness and partitioned between water and ether. The ether phase was washed with several portions of water, dried and concentrated to an oil (4.5 g.)

B. (L)-N-(1-benzyloxycarbonyl-2-phenylethyl)-(L)-phenylalanine, (R,S)-2,2-dimethyl-1,3-dioxalan-4-methyl ester The above product (4.4 g, 10 mmol) and R,S-2,2-dimethyl-1,3-dioxolan-4-methanol (2.5 ml, 20 mmol) were combined. Triethylamine (1.4 ml, 10 mmol) and N,N,-dimethylaminopyridine (20 mg) were added, and the mixture stirred under nitrogen at 55°-60° C. for 16 hrs. The reaction product was diluted with water and extracted with several portions of ether. The combined ether extracts were washed several times with water, dried, and concentrated to an oil (5.7 g). This material was chromatographed on 400 g silica gel, eluting with ethyl acetate-hexane (1:3). Fractions containing pure product were combined and evaporated to give 4.2 g material, $[\alpha]D^{26} - 6.2°$ (c=1, DMF), as an oil.

C. N-[L-[1-(R,S)-(2,2-dimethyl-1,3-dioxolan-4-yl)methoxy]carbonyl]-2-phenylethyl]-L-phenylalanine The preceding product (4.0 g, 7.7 mmol) was dissolved in some tetrahydrofuran and hydrogenated on a Parr apparatus over 0.4 g of 10% Pd-C at 60 psig for 4 hr. Catalyst was filtered, and the filtrate concentrated to give a waxy solid which was cystallized from ethyl acetate to give 2.6 g product, m.p 140°-142° C., $[\alpha]D^{26}$ 3.1° (c=1, DMF).

D. N-[N-[(L)-[1-(R,S)-(2,2-dimethyl-1,3-dioxolan-4-yl)-methoxy]-carbonyl]-2-phenylethyl]-(L)-phenylalanyl]-(R)-2-hydroxy-α-alanine,benzyl ester To a mixture of the preceding product (1.0 g, 2.3 mmol), R-isoserine benxzyl ester hydrochloride (625 mg, 2.7 mmol), 1-hydroxybenzotriazole hydrate (352 mg, 2.3 mmol), 1-(3-dimethylaminopropyl)-3-ethylcarbodiimide (440 mg, 2.3 mmol) and 15 ml dimethylformamide was added 0.95 ml (7.5 mmol) of N-ethylmorpholine. The mixture was stirred 4 hrs at room temperature. The mixture was poured into ice-water and extracted with several portions of ether. The combined extracts were washed with water, dried and concentrated to an oil (1.4 g). Chromatography on 120 g of silica gel eluting with ethyl acetate-hexane (2:1) gave 1.1 g of pure material as an oil, $[\alpha]D^{26} - 13.3°$ [c=1, DMF).

The R-isoserine benzyl ester hydrochloride used in the above procedure is prepared as follows:

A stirred suspension of N-[(p-methoxy)benzyloxy]-carbonyl-R-isoserine (12.4 g, 46 mmol) in 100 ml of benzyl alcohol was treated dropwise with thionyl chloride (13 ml) at 0°-5° C. The resulting solution was stirred at room temperature for 20 hrs. The resulting solution was then diluted with 350 ml of anhydrous ether, and the precipitated solids filtered and washed with ether. Recrystallization from isopropanol-ether gave 9.1 g product, m.p. 134°-50° C., $[\alpha]D^{26}16.6°$ (c=1, $H_2O$).

E.
N-[N-[(L)-[1-(R,S)-(2,2-dimethyl-1,3-dioxolan-4-yl)-methoxy]-carbonyl]-2-phenylethyl]-(L)-phenylalanyl]-(R)-2-hydroxy-β-alanine The preceding product (750 mg) was dissolved in 50 ml of ethanol and hydrogenated over 50 mg of 10% Pd/C at 50 psig for 4 hr. Catalyst was filtered and washed well with methylene chloride. The combined filtrates were concentrated to a gum which crystallized on standing for several hours under ether-hexane. Filter crystals to give 503 mg, m.p 125°–8° C. $[\alpha]_D^{26} -16.7°$ (c=1, DMF)

EXAMPLE 10
N-[N-[(L)-[1-(R,S)-(2,2-dimethyl-1,3-dioxolan-4-yl)-methoxy]-carbonyl]-2-phenylethyl]-(L)-phenylalanyl]-β-alanine

A.
N-[N-[(L)-[1-(R,S)-(2,2-dimethyl-1,3-dioxolan-4-yl)-methoxy]-carbonyl]-2-phenylethyl]-(L)-phenylalanyl]-β-alanine, benzyl ester The product of example 9C (2.5 g, 5.8 mmol), β-alanine benzyl ester p-toluenesulfonate (2.2 g., 6.4 mmol), 1-hydroxybenzotriazole hydrate (887 mg., 5.8 mmol), 1-(3-dimethylaminopropyl)-3-ethylcarbodiimide hydrochloride (1.1 g., 5.8 mmol), and N-ethylmorpholine (2.3 ml., 18 mmol) in 20 ml. of dimethylformamide was stirred at room temperature overnight. The resulting solution was poured into water and extracted with several portions of ether. The combined ether layers were washed repeatedly with water, dried, and concentrated to an oil (3.3 g.). This material was chromatographed on 300 g of silica gel eluting with ethyl acetate-hexane (1:2) to give 2.7 g of pure product, $[\alpha]_D^{26} -15.5°$ (c=0.75, DMF).

B.
N-[N-[(L)-[1-(R,S)-(2,2-dimethyl-1,3-dioxolan-4-yl)-methoxy]-carbonyl]-2-phenylethyl]-(L)-phenylalanyl]-β-alanine The product of the preceding example (2.2 g) was dissolved in 50 ml. of ethanol and hydrogenated over 0.2 g of 10% Pd/C at 50 psig for 4 hr. The catalyst was filtered and the filtrate concentrated to an oil (1.9 g) which solidified. Recrystallization from cold ether (−80° C.) gave 1.3 g solid, m.p. 80°–82° C., $[\alpha]_D^{26} -22.7°$ (c=1, DMF).

A maleate was prepared by dissolving 5.0 g of the above free base in 200 ml. of ether and treating with maleic acid (1.16 g) dissolved in 200 ml. ether. Crystals slowly formed on standing overnight. These were filtered and dried to give 4.7 g crystals, mp 127°–9° C., $[\alpha]_D^{26} -16.3°$ [c=1, DMF). This salt was found to be a 1 to 1 salt, base to maleic acid, and may be referred to as either the maleate salt or the hemimaleate salt.

Analysis calculated for $C_{27}H_{34}N_2O_7$, $C_4H_4O_4$: C, 60.58; H, 6.23; N, 4.55. found: C, 60.33; H, 6.31; N, 4.48.

Recrystallization of this material from acetonitrile raised the melting point to 132°–134° C. $[\alpha]_D^{26} -15.9°$ (c=1, DMF).

Analysis found C, 60.74; H, 6.10; N, 4.39.

I claim:

1. A method for inhibiting the action of enkephalinases in a mammal to thereby elicit an analgesic effect in said mammal, which method comprises administering an enkephalinase inhibitory effective amount of a compound having structural formula I

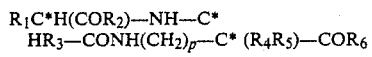

or a racemate, enantiomer and diasterioisomer thereof or a pharmaceutically acceptable salts thereof to said mammal wherein:

$R_1$ is alkyl having from 1to 6 carbon atoms, adamantylmethyl, cycloakylmethyl having from 4 to 8 carbon atoms or $A-X_m-C_nH_{2n}$—wherein X is oxygen or sulfur, A is phenyl which may be substituted with the group, Y, wherein Y is halogen, hydroxy, trifluoromethyl, alkoxy having from 1 to 6 carbon atoms, alkyl having from 1 to 6 carbon atoms, 2- and 3-furanyl, 2- and 3-thienyl, or phenyl {which may be substituted with halogen, hydroxy, trifluoromethyl, alkoxy having from 1 to 6 carbon atoms or alkyl having from 1 to 6 carbon atoms) benzyl {the phenyl ring of which may be substituted with the group, Y, as defined herein}, 1- and 2-naphthyl, 2-and 3-furanyl or 2- and 3-thienyl; m is 0 or 1 and n is 0, 1, 2, 3, or 4;

$R_2$ and $R_6$ may be the same or different and are hydroxy, alkoxy having from 1 to 8 carbon atoms, $B-X_m-C_nH_{2n}-O$—wherein B is phenyl {which may be substituted with the group, Y, as defined herein}or 1- and 2-naphthyl, X, m, and n are as defined herein provided that when n=0, m=0, —OCH$_2$OCO-alkyl having from 3 to 8 carbon atoms, —OCH$_2$CO-phenyl {the phenyl ring of which may be substituted with the group, Y, as defined herein}, 1-glyceryl,

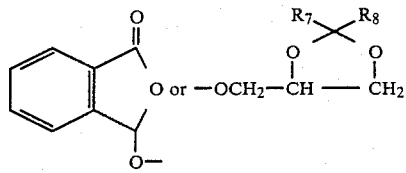

wherein $R_b$ 7 is hydrogen, alkyl having from 1 to 6 carbon atoms, or phenyl which may be substituted with the group, Y, as defined herein, and $R_8$ is hydrogen or alkyl having from 1 to 6 carbon atoms;

$R_2$ may also —$NR_7R_8$ wherein $R_7$ and $R_8$ are as defined herein;

$R_3$ is alkyl having from 1 to 6 carbon atoms, cycloalkylmethyl having from 4 to 8 carbon atoms, 2- and 3-thienylmethyl, 2- and 3-furanylmethyl, 1- and 2-naphthylmethyl, or benzyl the phenyl ring of which may be substituted with the group, Y, as defined herein;

$R_4$ is D—$C_nH_{2n}-O_m$—wherein D is hydrogen, alkyl having from 1 to 4 carbon atoms or phenyl which may be substituted with the group, Z, wherein Z is halogen, hydroxy, trifluoromethyl, alkoxy having from 1 to 6 carbon atoms, or alkyl having from 1 to 6 carbon atoms; m and n are as defined herein;

$R^4$ may also be —$NR_5COR_7$ {wherein $R_5$ and $R_7$ are defined herein}, and —$NR_5CO_2R_9$ {wherein $R_5$ is defined herein and $R_9$ is alkyl having from 1 to 6 carbon atoms or phenyl which may be substituted with the group Y, as defined herein} provided that p is 1 or 2;

$R_5$ is hydrogen or alkyl having from 1 to 6 carbon atoms; and
p is 0, 1 or 2.

2. The method defined in claim 1 wherein
$R_1$ is benzyl, p-chlorobenzyl, p-methoxybenzyl, p-methylbenzyl, p-phenylbenzyl, 2-phenylethyl or 1- and 2-naphthylmethyl;
$R_2$ and $R_6$ may be the same or different and are hydroxy, methoxy, ethoxy, benzyloxy, 2-phenoxyethoxy,
1-glyceryl,

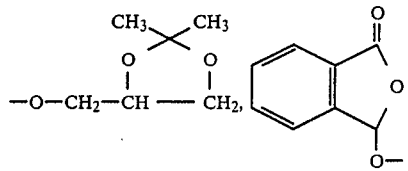

or pivaloyloxymethoxy;
$R_3$ is benzyl p-methylbenzyl, p-phenylbenzyl, 1-naphthylmethyl or 3-thienylmethyl;
$R_4$ is hydrogen, methyl or benzyl;
$R_5$ is hydrogen; and
p is 1 or 2.

3. The method defined in claim 1 wherein
$R_1$ is benzyl or p-phenylbenzyl;
$R_2$ is hydroxy, 2-phenoxyethoxy, 1-glyceryl,

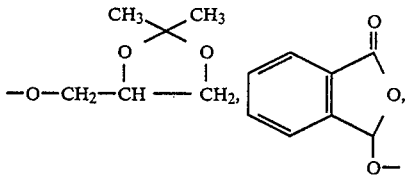

pivaloyloxymethoxy or benzyloxy;
$R_3$ is benzyl or p-phenylbenzyl;
$R_4$ is hydrogen, methyl or benzyl;
$R_5$ is hydrogen;
$R_6$ is hydroxy; and
p is 1.

4. The method defined in claim 2 wherein $R_2$ is 2-phenoxy-ethoxy, 1-glyceryl, pivaloyloxymethoxy,

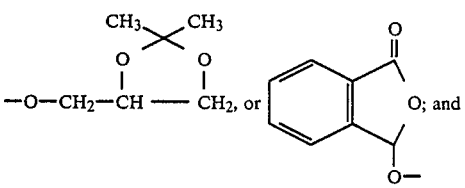

$R_6$ is hydroxy.

5. The method defined in claim 2 wherein $R_2$ is hydroxy and $R_6$ is 2-phenoxyethoxy, 1-glyceryl, pivaloyloxymethoxy,

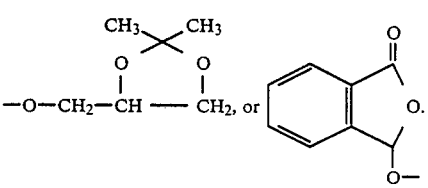

6. The method defined in claim 1 wherein p is 1.
7. A method as defined in claim 1 wherein the compound administered has the name:
N-[N-[(L-1-carboxy-2-phenylethyl)]-L-phenyl-alanyl]-β-alanine;
N-[N-[L-1-(2,2-dimethyl-1-oxopropoxy)-methoxy]-carbonyl]-2-phenylethyl]-L-phenylalanyl]-alanine, (2,2-dimethyl-1-oxopropoxy)methyl ester;
N-[N-[L-1-[phenylmethoxy]carbonyl]-2-phenyl-ethyl]-L-phenylalanyl]-β-alanine, (2,2-dimethyl-1-oxopropoxy)methylester;
N-[N-[L-1-carboxy-2-(4-phenyl)phenylethyl]-L-phenylalanyl]-β-alanine;
N-[N-[L-[1-[(2,2-dimethyl-1-oxopropoxy)-methoxy]-carbonyl]-2-(4-phenyl)phenylethyl]-L-phenylalanyl]-β-alanine,(2,2-dimethyl-1-oxopropoxy)methyl ester;
N-[N-[L-1-carboxy-2-phenylethyl]-L-(4-phenyl)-phenylalanyl]-8-alanine;
N-[N-[L-[1-[(2,2-dimethyl-1-oxopropoxy)-methoxycarbonyl]-2-(4-phenyl)phenylethyl]-L-(4-phenyl)-phenylalanyl-βalanine, (2,2-dimethyl-1-oxopropoxy)-methyl ester;
N-[N-[L-[1-[(2,2-dimethyl-1-oxopropoxy)-methoxy]-carbonyl]-2-phenylethyl]-L-(4-phenyl)phenylalanyl]-β-alanine, (2,2-dimethyl-1-methyl ester;
N-[N-[L-1-carboxy-2-phenylethyl]-L-phenylalanyl]-L-(1-methyl)-β-alanine;
N-[N-[L-[1-[(2,2-dimethyl-1-oxopropoxy)methoxy]-carbonyl]-2-phenylethyl]-L-phenylalanyl]-L-(1-methyl)-β-alanine,(2,2-dimethyl-1-oxopropoxy)-methyl ester;
N-[N-[(L-1-carboxy-2-phenylethyl)]-L-phenylalanyl]-β-alanine, 2-phenoxyethyl ester;
N-[N-[(D-1-carboxy-2-phenylethyl)]-L-leucyl]-L-phenylalanine;
N-[N-[(L-1-carboxy-2-phenylethyl)]-L-phenylalanyl]-L-phenylalanine;
N-[N-[(L-1-carboxy-3-phenylpropyl)]-L-phenylalanyl]-β-alanine;
N-[N-[L-[1-[(2,2-dimethyl-1-oxopropoxy)-methoxy]-carbonyl]-2-phenylethyl]-L-phenylalanyl]-β-alanine;
N-[N-[L-[1-[(2-phenoxy)ethoxy]carbonyl]-2-phenylethyl]-L-phenylalanyl]-β-alanine;
N-[N-[L-[1-[(1-oxo-3-isobenzofuranyloxy)]-carbonyl]-2-phenylethyl]-L-phenylalanyl-β-alanine;
N-[N-[L-[1-[(2,3-dihydroxy)-1-propoxy]-carbonyl]-2-phenylethyl]-L-phenylalanyl]-β-alanine;
N-[N-[L-[1-[(2,2-dimethyl-1,3-dioxolan-4-yl)methoxy]-carbonyl]-2-phenylethyl]-L-phenylananyl]-β-alanine;
N-[N-[L-[1-[(2,2-dimethyl-1-oxypropoxy)methoxy]-carbonyl]-2-(4-phenyl)phenylethyl]-L-phenylalanyl]-β-alanine;
N-[N-[L-[1-[(2-phenoxy)ethoxy]carbonyl]-2-(4-phenyl)-phenylethyl]-L-phenylalanyl]-β-alanine;
N-[N-[L-[1-[(1-oxo-3-isobenzofuranyloxy)]-carbonyl]-2-(4-phenyl)phenylethyl]-L-phenylalanyl]-β-alanine;
N-[N-[L-[1-[(2,3-dihydroxy)-1-propoxy]-carbonyl]-2-(4-phenyl)phenylethyl]-L-phenylalanyl]-β-alanine;
N-[N-[L-[1-[(2,2-dimethyl-1,3-dioxolan-4-yl)-methoxy]-carbonyl]-2-(4-phenyl)phenylethyl]-L-phenylalanyl]-β-alanine;
N-[N-[L-[1-[(2,2-dimethyl-1-oxypropoxy)methoxy]-carbonyl]-2-phenylethyl]-L-(4-phenyl)phenylalanyl]-β-alanine;
N-[N-[L-[1-[(2-phenoxy)ethoxy]carbonyl]-2-phenylethyl]-L-(4-phenyl)phenylalanyl]-β-alanine;
N-[N-[L-[1-[(1-oxo-3-isobenzofuranyloxy)]-carbonyl]-2-phenylethyl]-L-(4-phenyl)phenylalanyl]-β-alanine;

N-[N-[L-[1-[(2,3-dihydroxy)-1-propoxy]-carbonyl]-2-phenylethyl]-L-(4-phenyl)phenylalanyl]-β-alanine;

N-[N-[L-[1-[(2,2-dimethyl-1,3-dioxolan-4-yl)methoxy]-carbonyl]-2-phenylethyl]-L-(4-phenyl)-phenylalanyl]-β-alanine;

N-[N-[L-[1-[(2,2-dimethyl-1-oxypropoxy)-methoxy]-carbonyl]-2-(4-phenyl)phenylethyl]-L-(4-phenyl)-phenylalanyl]-β-alanine;

N-[N-[L-[1-[(2-phenoxy)ethoxy]carbonyl]-2-(4-phenyl)phenylethyl]-L-(4-phenyl)phenylalanyl]-β-alanine;

N-[N-[L-[1-[(1-oxo-3-isobenzofuranyloxy)]-carbonyl]-2-(4-phenyl)phenylethyl]-L-(4-phenyl)phenylalanyl]-β-alanine;

N-[N-[L-[1-[2,3-dihydroxy)-1-propoxy]-carbonyl]-2-(4-phenyl)-phenylethyl]-L-(4-phenyl)-phenylalanyl]-β-alanine;

N-[N-[L-[1-[(2,2-dimethyl-1,3-dioxolan-4-yl) -yl-methoxy-carbonyl]-2-(4-phenyl)phenylethyl]-L-(4-phenyl)-phenylalanyl]-β-alanine;

N-[N-[L-[1-[(2,2-dimethyl-1-oxypropoxy)-methoxy]-carbonyl]-2-phenylethyl]-L-phenylalanyl]-D,L-α-methyl-β-alanine;

N-[N-[L-[1-[(2-phenoxy)ethoxy]carbonyl]-2-phenylethyl]-L-phenylalanyl]-D,L-α-methyl-β-alanine;

N-[N-[L-[1-[(1-oxo-3-isobenzofuranyloxy)]-carbonyl]-2-phenylethyl]-L-phenylalanyl]-D,L-α-methyl-β-alanine;

N-[N-[L-[1-[(2,3-dihydroxy)-1-propoxy]-carbonyl]-2-phenylethyl]-L-phenylalanyl]-D,L-α-methyl-α-alanine;

N-[N-[L-[1-[(2,2-dimethyl-1,3-dioxolan-4-yl)-methoxy]-carbonyl]-2-phenylethyl]-L-phenylalanyl]-D,L-α-methylβ-alanine;

N-[N-[L-[1-[(2,2-dimethyl-1-oxypropoxy)-methoxy]-carbonyl]-2-(4-phenyl)phenylethyl]-L-phenylalanyl]-D,L-α-methyl-β-alanine;

N-[N-[L-[1-[(2-phenoxy)ethoxy]carbonyl]-2-(4-phenyl)-phenylethyl]-L-phenylalanyl]-D,L-α-methyl-βalanine;

N-[N-[L-[1-[(1-oxo-3-isobenzofuranyloxy)]-carbonyl]-2-(4-phenyl)phenylethyl]-L-phenylalanyl]-D,L-α-methyl-β-alanine;

N-[N-[L-[1-[(2,3-dihydroxy)-1-propoxy]carbonyl]-2-(4-phenyl)phenylethyl]-L-phenylalanyl]-D,L-α-methyl-βalanine;

N-[N-[L-[1-[(2,2-dimethyl-1,3-dioxolan-4-yl)-methoxy]-carbonyl]-2-(4-phenyl)phenylethyl]-L-phenylalanyl]-D,L-α-methyl-β-alanine;

N-[N-[L-[1-[(2,2-dimethyl-1-oxypropoxy)methoxy]-carbonyl]-2-phenylethyl]-L-(4-phenyl)phenylalanyl]-D,L-α-methyl-β-alanine;

N-[N-[L-[1-[(2-phenoxy)ethoxy]carbonyl]-2-phenylethyl]-L-(4-phenyl)phenylalanyl]-D,L-α-methyl-β-alanine;

N-[N-[L-[1-[(1-oxo-3-isobenzofuranyloxy)]-carbonyl]-2-phenylethyl]-L-(4-phenyl)phenylalanyl]-D,L-α-methyl-β-alanine;

N-[N-[L-[1-[(2,3-dihydroxy)-1-propoxy]carbonyl-2-phenylethyl]-L-(4-phenyl)phenylalanyl]-D,L-α-methyl-β-alanine;

N-[N-[L-[1-[(2,2-dimethyl-1,3-dioxolan-4-yl)-methoxy]-carbonyl]-2-phenylethyl]-L-(4-phenyl)phenylalanyl]-D,L-α-methyl-β-alanine;

N-[N-[L-[1-[(2,2-dimethyl-1-oxypropoxy)methoxy]-carbonyl]-2-(4-phenyl)phenylethyl]-L-(4-phenyl)-phenylalanyl]-D,L-α-methyl-β-alanine;

N-[N-[L-[1-[(2-phenoxy)ethoxy]carbonyl]-2-(4-phenyl)-phenylethyl]-L-(4-phenyl)phenylalanyl]-D,L-α-methyl-β-alanine;

N-[N-[L-[1-[(1-oxo-3-isobenzofuranyloxy)]carbonyl]-2-(4-phenyl)phenylethyl]-L-(4-phenyl)phenylalanyl]-D,L-α-methyl-β-alanine;

N-[N-[L-[1-[(2,3-dihydroxy)-1-propoxy]carbonyl]-2-(4-phenyl)phenylethyl]-L-(4-phenyl)-phenylalanyl]-D,L-α-methyl-β-alanine;

N-[N-[L-[1-[(2,2-dimethyl-1,3-dioxolan-4-yl)-methoxy]-carbonyl]-2-(4-phenyl)phenylethyl]-L-(4-phenyl)-phenylalanyl]-D,L-α-methyl-β-alanine;

N-[N-[L-[1-[(2,2-dimethyl-1-oxypropoxy)-methoxy]-carbonyl]-2-phenylethyl]-L-2-thienylalanyl]-β-alanine;

N-[N-[L-[1-[(2,2-dimethyl-1-oxypropoxy)-methoxy]-carbonyl]-2-phenylethyl]-L-3-thienylalanyl]-β-alanine;

N-[N-[L-[1-[(2,2-dimethyl-1-oxypropoxy)methoxy]carbonyl]-2-phenylethyl]-L-2-furoalanyl]-β-alanine;

N-[N-[L-[1-[(2,2-dimethyl-1-oxypropoxy)methoxy]carbonyl]-2-phenylethyl]-L-phenylalanyl]-α-methylalanine;

N-[N-[L-[1-[(2,2-dimethyl-1-oxypropoxy)methoxy]carbonyl]-2-phenylethyl]-L-phenylalanyl]-L-α-hydroxy-β-alanine;

N-[N-[L-[1-[(2,2-dimethyl-1-oxypropoxy)methoxy]carbonyl]-2-phenylethyl]-L-phenylalanyl]-D-α-hydroxy-β-alanine;

N-[N-[L-[1-[(2,2-dimethyl-1-oxypropoxy)methoxy]carbonyl]-2-phenylethyl]-L-phenylalanyl]-L-β-methoxy-β-alanine;

N-[N-[L-[1-[(2,2-dimethyl-1-oxypropoxy)methoxy]carbonyl]-2-phenylethyl]-L-phenylalanyl]-D-α-methoxy-β-alanine;

N-[N-[L-[1-[(2,2-dimethyl-1-oxypropoxy)methoxy]carbonyl]-2-phenylethyl]-L-phenylalanyl]-D-α-hydroxy-β-alanine;

N-[N-[L-[1-[(2,2-dimethyl-1-oxypropoxy)methoxy]carbonyl]-2-phenylethyl]-L-phenylalanyl]-L-α-methoxy-β-alanine;

N-[N-[L-[1-[(2,2-dimethyl-1-oxypropoxy)methoxy]carbonyl]-2-phenylethyl]-L-phenylalanyl]-D-α-methoxy-β-alanine;

N-[N-[L-[1-[(2,2-dimethyl-1,3-dioxolan-4-yl)-methoxy]-carbonyl]-2-phenylethyl]-L-phenylalanyl]-R-α-hydroxy-β-alanine;

N-[N-[L-[1-[(2,2-dimethyl-1,3-dioxolan-4-yl)-methoxy]-carbonyl]-2-phenylethyl]-(L)-phenylalanyl]-62 -alanine, hemimaleate;

N-[N-[(L)1-carboxy-2-phenylethyl)]-L-phenyl-alanyl]-S-2-[N-[(1,1-dimethylethoxy)carbonyl]amino-β-alanine; or a pharmaceutically acceptable salt of such a compound.

8. The method as defined in claim 1 wherein the compound aministered has the name N-[N-[(L)-[1-[(2,2-dimethyl-1,3-dioxolan-4-yl)-methoxy]-carbonyl]-2-phenylethyl]-L-phenylalanyl]-β-alanine, or a diastereoisomer and/or pharmaceutically acceptable salt thereof.

9. The method as defined in claim 8 wherein the compound is in the form of a 1 to 1 salt with maleic acid.

10. The method as defined in claim 1 wherein the compound administered has the name N-[N-[L-[1-(2,2-dimethyl-1,3-dioxolan-4-yl)-methoxy]-carbonyl]-2-7 phenylethyl]-L-phenylalanyl]-R-α-hydroxy-β-alanine, or a pharmaceutically acceptable salt thereof.

11. The method as defined in claim 1 wherein the compound adminstered has the name N-[N-[(L-1-carboxy-2-phenyl)ethyl]-L-phenylalanyl-β-alanine, or a a diasterioisomer and/or pharmaceutically acceptable salt thereof.

12. A pharmaceutical composition useful for inhibiting the action of enkephalinases in a mammal, which composition comprises a compound having the structural formula I as defined in claim 1 in combination with a pharmaceutically acceptable carrier.

13. A harmaceutical composition according to claim 12 wherein the compound is a compound as defined in claim 2, 3, 4, or 7.

14. A pharmaceutical composition according to claim 12 wherein the compound comprises N-[N-[(L)-[1-(2,2-dimethyl-1,3-dioxolan-4-yl)methoxy]carbonyl]-2-phenylethyl]-L-phenylalanyl]-8-alanine or a diasterioisomer and/or pharmaceutically acceptable salt thereof.

15. A pharmaceutical composition according to claim 12 wherein the compound comprises N-[N-[(L-1-carboxy-2-phenyl)ethyl-L-phenylalanyl]-β-alanine or a pharmaceutically acceptable salt thereof.

* * * * *